(12) United States Patent
Sweeney

(10) Patent No.: US 6,654,638 B1
(45) Date of Patent: Nov. 25, 2003

(54) ULTRASONICALLY ACTIVATED ELECTRODES

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/545,104

(22) Filed: Apr. 6, 2000

(51) Int. Cl.$^7$ ............................................... A61N 1/362
(52) U.S. Cl. ........................ 607/9; 607/2; 607/33; 607/36
(58) Field of Search .......................... 607/9, 10, 2, 32, 607/33, 34, 35, 36, 60, 116, 119, 122

(56) References Cited

U.S. PATENT DOCUMENTS

| | | | | |
|---|---|---|---|---|
| 3,456,134 A | * | 7/1969 | Ko ................................. 310/319 |
| 3,552,382 A | * | 1/1971 | Mount .......................... 600/453 |
| 3,659,615 A | * | 5/1972 | Enger .......................... 174/52.4 |
| 3,835,864 A | * | 9/1974 | Rasor et al. ................. 607/126 |
| 3,867,950 A | * | 2/1975 | Fischell ........................ 320/137 |
| 4,481,950 A | | 11/1984 | Duggan ........................ 128/419 |
| 4,561,444 A | * | 12/1985 | Livingston et al. ........... 607/30 |
| 4,600,017 A | | 7/1986 | Schroeppel ................... 128/784 |
| 4,690,143 A | * | 9/1987 | Schroeppel ...................... 607/5 |
| 4,706,681 A | | 11/1987 | Breyer et al. ................ 128/642 |
| 4,770,177 A | | 9/1988 | Schroeppel ................... 128/419 |
| 4,886,064 A | * | 12/1989 | Strandberg ................... 128/903 |
| 4,896,068 A | * | 1/1990 | Nilsson ........................ 310/329 |
| 4,945,898 A | | 8/1990 | Pell et al. ....................... 128/24 |
| 5,065,761 A | | 11/1991 | Pell ........................... 128/660.03 |
| 5,113,859 A | | 5/1992 | Funke ............................ 128/419 |
| 5,139,020 A | | 8/1992 | Koestner et al. ......... 128/419 PG |
| 5,156,148 A | | 10/1992 | Cohen ............................ 128/419 |
| 5,156,154 A | | 10/1992 | Valenta, Jr. et al. ..... 128/661.09 |
| 5,156,157 A | | 10/1992 | Valenta, Jr. et al. ......... 128/662 |
| 5,158,071 A | | 10/1992 | Umemura et al. ............. 128/24 |

(List continued on next page.)

Primary Examiner—Kennedy Schaetzle
(74) Attorney, Agent, or Firm—Schwegman, Lundberg, Woessner & Kluth, P.A.

(57) ABSTRACT

An implantable electrode, where the electrode comprises a first piezoelectric element which converts mechanical energy into electrical energy, and a cathode and an anode, where electrical energy generated by the first piezoelectric element causes a pacing level energy pulse to be delivered between the anode and the cathode. The mechanical energy for stimulating the piezoelectric element originates from a source external to the implantable electrode. In one embodiment, the external source is from a transmitter that is located on, or integrated into, either a cardiac lead and/or the implantable pulse generator. The electrode further includes an implantable housing into which is integrated the first piezoelectric element and on which is mounted the anode and the cathode. The housing also contains pacing control circuitry, which is coupled to the first piezoelectric element, the anode and the cathode. In one embodiment, the pacing control circuitry serves to receive the electrical energy generated by the first piezoelectric element and control the delivery of pacing level energy pulse between the anode and the cathode.

17 Claims, 7 Drawing Sheets

U.S. PATENT DOCUMENTS

| | | | |
|---|---|---|---|
| 5,183,040 A | 2/1993 | Nappholz et al. | 128/419 PG |
| 5,188,106 A | 2/1993 | Nappholz et al. | 128/419 PG |
| 5,243,976 A | 9/1993 | Ferek-Petric et al. | 607/6 |
| 5,271,408 A | 12/1993 | Breyer et al. | 128/673 |
| 5,311,095 A | 5/1994 | Smith et al. | 310/334 |
| 5,316,001 A | 5/1994 | Ferek-Petric et al. | 128/661.08 |
| 5,318,595 A | 6/1994 | Ferek-Petric et al. | 607/17 |
| 5,329,496 A | 7/1994 | Smith | 367/140 |
| 5,330,505 A | 7/1994 | Cohen | 607/6 |
| 5,409,002 A | 4/1995 | Pell | 128/653.1 |
| 5,409,009 A | 4/1995 | Olson | 128/661.08 |
| 5,411,535 A | 5/1995 | Fujii et al. | 607/32 |
| 5,548,564 A | 8/1996 | Smith | 367/140 |
| 5,674,258 A | 10/1997 | Henschel et al. | 607/19 |
| 5,744,898 A | 4/1998 | Smith et al. | 310/334 |
| 5,749,909 A | 5/1998 | Schroeppel et al. | 607/33 |
| 5,799,350 A | 9/1998 | Ferek-Petric et al. | 607/17 |
| 5,807,258 A | 9/1998 | Cimochowski et al. | 600/454 |
| 5,814,089 A | 9/1998 | Stokes et al. | 607/32 |
| 5,861,018 A * | 1/1999 | Feierbach | 128/899 |
| 5,885,471 A | 3/1999 | Ruben et al. | 216/33 |
| 5,911,738 A | 6/1999 | Sikorski et al. | 607/19 |
| 5,967,986 A | 10/1999 | Cimochowski et al. | 600/454 |
| 5,967,989 A | 10/1999 | Cimochowski et al. | 600/459 |
| 5,990,598 A | 11/1999 | Sudol et al. | 310/334 |
| 6,020,675 A | 2/2000 | Yamahita et al. | 310/358 |
| 6,038,475 A | 3/2000 | Sikorski et al. | 607/19 |
| 6,141,588 A | 10/2000 | Cox et al. | 607/9 |
| 6,216,040 B1 * | 4/2001 | Harrison | 607/57 |
| 6,259,951 B1 * | 7/2001 | Kuzma et al. | 600/25 |

* cited by examiner

ULTRASONICALLY ACTIVATED ELECTRODES

FIELD OF THE INVENTION

This invention relates generally to medical devices, and more particularly to pulse generating systems.

BACKGROUND

Implantable pulse generators (e.g., pacemakers, implantable cardioverter/defibrillators) are integrated highly sophisticated electro-mechanical systems. They typically comprise at least one implantable cardiac lead coupled to a pulse generating device. The implantable cardiac leads serve to physically and electrically connect the pulse generating device, including the electronic circuitry housed within the device, to pacing electrodes positioned on the implantable cardiac lead. The implantable cardiac lead, therefore, acts as a tether to connect the pacing electrodes on the cardiac lead to the implantable pulse generating device.

Implantable cardiac leads typically include at least one pacing electrode, a lead conductor, lead insulation, and a lead connector. When one pacing electrode is present on the implantable cardiac lead, it is typically placed at the distal end of the lead. The lead conductor physically and electrically couples the pacing electrode to the electronic circuitry of the pulse generator. The lead conductor serves to conduct pacing level energy pulses from the electronic circuitry to the pacing electrode, and to conduct cardiac signals sensed by the pacing electrode to the electronic circuitry.

The lead conductor is housed within the lead insulation. The lead insulation electrically isolates the lead conductor, allowing the pacing level energy pulses from the pulse generator to be delivered to the pacing electrode and cardiac signals from the pacing electrode to be delivered to the electronic circuitry of the pulse generator. The lead connector also serves to physically couple the implantable cardiac lead to the housing of the pulse generator. Thus, the current state of the art for implantable pulse generators is to use the lead conductor to pass electrical pacing pulses to the pacing electrode when delivering pacing pulses to the heart.

The size of implantable cardiac leads is often a limiting factor in where the implantable cardiac lead can be positioned within the heart. Typically, implantable cardiac leads have been implanted through the venous side of the circulatory system, with the distal end of the cardiac lead being positioned in either the right ventricle or right atrium. Implantable cardiac leads can also be positioned adjacent the left atrium or left ventricle by placing the lead in the coronary sinus or great cardiac vein. Regardless of the location, the pacing electrodes are always tethered to the pulse generator by cardiac lead. As a result, sites available for cardiac pacing by implantable cardiac leads are limited. Thus, a need exists whereby implanted electrodes for delivering electrical energy to cardiac tissue need not be constrained by the presence of a cardiac lead.

SUMMARY OF THE INVENTION

The present subject matter removes the limitation of the pacing electrode being coupled, or tethered, to the implantable cardiac lead. In one embodiment, there are provided self-contained electrodes which are adapted to receive at least one signal from a transmitter. In response to receiving the at least one signal, the self-contained electrodes generate and deliver an electrical energy pulse. In one embodiment, the electrical energy pulses are pacing level energy pulses. Thus, the present subject matter allows for the physical connection between the implantable cardiac lead and the pacing electrode to be severed. By severing the physical connection between the implantable cardiac lead and the pacing electrode, the self-contained electrodes of the present subject matter are able to be placed at any number of locations within the cardiac tissue without the limiting constraint of the traditional implantable cardiac lead.

In one embodiment, present subject matter provides an implantable electrode, where the electrode comprises a first piezoelectric element which converts mechanical energy into electrical energy, and a cathode and an anode, where electrical energy generated by the first piezoelectric element causes a pacing level energy pulse to be delivered between the anode and the cathode. In one embodiment, the mechanical energy for stimulating the piezoelectric element originates from a source external to the implantable electrode. In one embodiment, the external source is from a transmitter that is located on, or integrated into, either a cardiac lead and/or the implantable pulse generator.

In one embodiment, the implantable electrode includes an implantable housing into which is integrated the first piezoelectric element. The housing also includes an anode and a cathode positioned the peripheral surface of the housing. The housing also contains pacing control circuitry, which is coupled to the first piezoelectric element, the anode and the cathode. In one embodiment, the pacing control circuitry serves to receive the electrical energy generated by the first piezoelectric element and control the delivery of pacing level energy pulse between the anode and the cathode.

In an additional embodiment, the implantable electrode can further include a potential energy source (e.g., an electrochemical cell) which supplies at least a portion of the energy necessary to pace the cardiac tissue. In addition to the potential energy source, the pacing control circuitry can further include a switch, where the switch is operated by the electrical energy generated by the first piezoelectric element. In one embodiment, the switch is activated so as to deliver a pulse between the anode and cathode when the switch receives electrical energy generated by the first piezoelectric element.

In an alternative embodiment, the implantable electrode can further include a second piezoelectric element which converts mechanical energy into electrical energy. When a first and second piezoelectric element are present, each element is selected to resonate in a different frequency range, so that the first piezoelectric element resonates at a first frequency range and the second piezoelectric element resonates at a second frequency range. The implantable electrode further includes both the switch and a capacitor. In one embodiment, the switch is coupled to the first piezoelectric element, the second piezoelectric element, the anode and the cathode, and the capacitor is coupled to the switch.

Electrical energy is generated by the first piezoelectric element when a first transmission at the first frequency range resonates the first piezoelectric element and electrical energy is generated by the second piezoelectric element when a second transmission at the second frequency range resonates the second piezoelectric element, where the electrical energy is stored in the capacitor. The switch is then used to cause the pacing level energy pulse to be delivered between the anode and the cathode when a predetermined pulse signal is detected. In one embodiment, the predetermined pulse signal is a predetermined frequency change in the first frequency range. Alternatively, the predetermined pulse signal is a predetermined frequency change in the first and second frequency ranges.

In an alternative embodiment, the pacing control circuitry includes a switch, where the switch is operated by the electrical energy generated by the first piezoelectric element, and a potential energy source, where the potential energy source is coupled to the switch and supplies electrical energy to be delivered between the anode and the cathode once the first piezoelectric element provides electrical energy to activate the switch.

These and other features and advantages of the invention will become apparent from the following description of the preferred embodiments of the invention.

DETAILED DESCRIPTION

Figure 1:
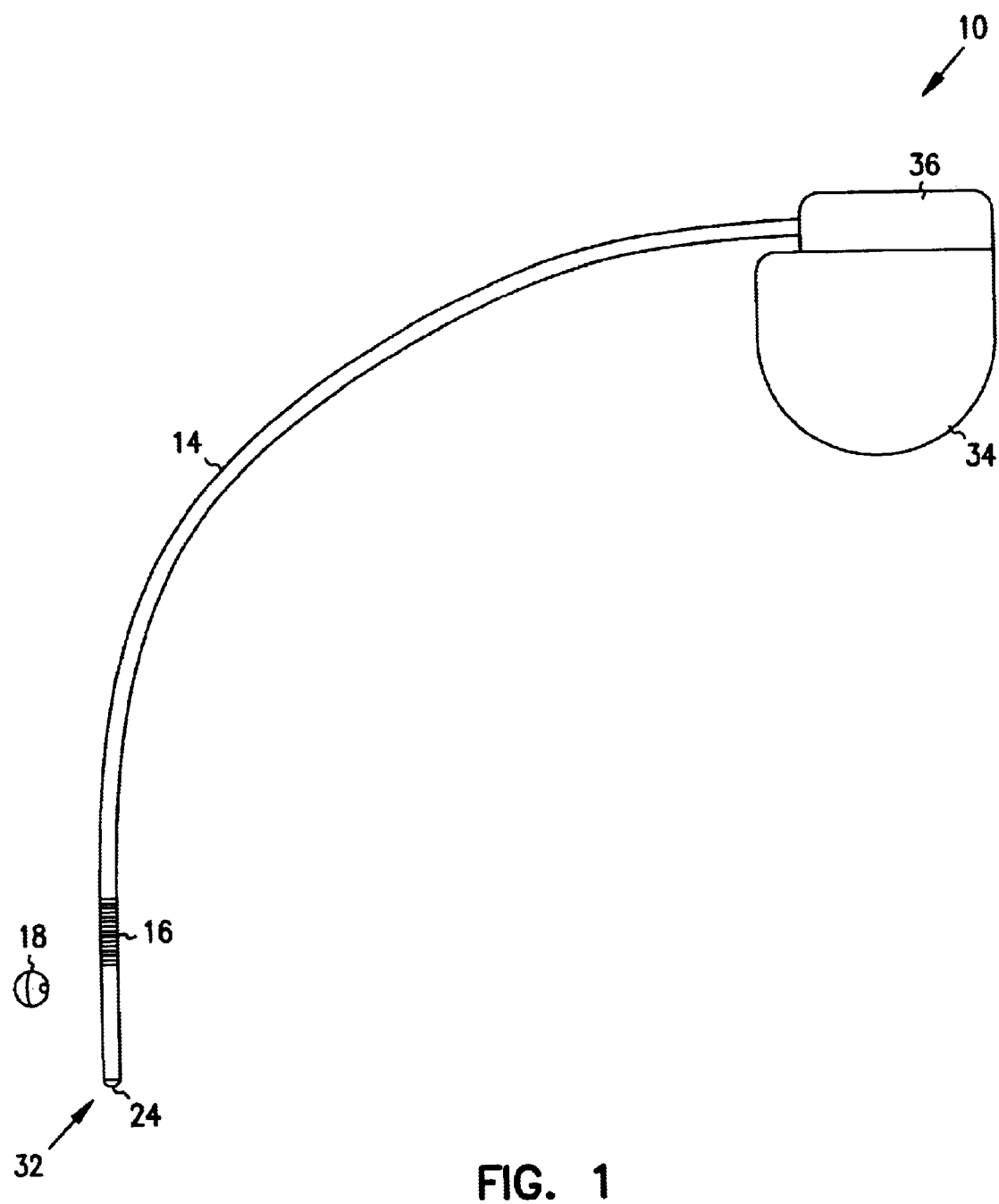
FIG. 1 shows one embodiment of a system according to the present subject matter.

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Implantable pulse generators (e.g., pacemakers, implantable cardioverter/defibrillators) are integrated highly sophisticated electro-mechanical systems. They typically comprise at least one implantable cardiac lead coupled to a pulse generating device. The implantable cardiac leads serve to physically and electrically connect the pulse generating device, including the electronic circuitry housed within the device, to pacing electrodes positioned on the implantable cardiac lead. The implantable cardiac lead, therefore, acts as a tether to connect the pacing electrodes on the cardiac lead to the implantable pulse generating device.

Implantable cardiac leads typically include at least one pacing electrode, a lead conductor, lead insulation, and a lead connector. When one pacing electrode is present on the implantable cardiac lead, it is typically placed at the distal end of the lead. The lead conductor physically and electrically couples the pacing electrode to the electronic circuitry of the pulse generator. The lead conductor serves to conduct pacing level energy pulses from the electronic circuitry to the pacing electrode, and to conduct cardiac signals sensed by the pacing electrode to the electronic circuitry.

The lead conductor is housed within the lead insulation. The lead insulation electrically isolates the lead conductor, allowing the pacing level energy pulses from the pulse generator to be delivered to the pacing electrode and cardiac signals from the pacing electrode to be delivered to the electronic circuitry of the pulse generator. The lead connector also serves to physically couple the implantable cardiac lead to the housing of the pulse generator. Thus, the current state of the art for implantable pulse generators is to use the lead conductor to pass electrical pacing pulses to the pacing electrode when delivering pacing pulses to the heart.

The size of implantable cardiac leads is often a limiting factor in where the implantable cardiac lead can be positioned within the heart. Typically, implantable cardiac leads have been implanted through the venous side of the circulatory system, with the distal end of the cardiac lead being positioned in either the right ventricle or right atrium. Implantable cardiac leads can also be positioned adjacent the left atrium or left ventricle by placing the lead in the coronary sinus or great cardiac vein. Regardless of the location, the pacing electrodes are always tethered to the pulse generator by cardiac lead. As a result, sites available for cardiac pacing by implantable cardiac leads are limited.

The present subject matter relates to a system that removes the limitation of a pacing electrode being coupled, or tethered, to an implantable cardiac lead. In one embodiment, there are provided self-contained electrodes which are adapted to receive at least one signal from a transmitter. In response to receiving the at least one signal, the self-contained electrodes generate and deliver to the heart an electrical energy pulse. In one embodiment, the electrical energy pulses are pacing level energy pulses. Thus, the present subject matter allows for the physical connection between the implantable cardiac lead and the pacing electrode to be severed. By severing the physical connection between the implantable cardiac lead and the pacing electrode, the self-contained electrodes of the present subject matter are able to be placed at any number of locations within the cardiac tissue without the limiting constraint of the traditional implantable cardiac lead.

FIG. 1 shows an embodiment of a system of the present subject matter. The system includes an implantable pulse generator 10 to which is physically and electrically coupled a transvenous catheter 14. In one embodiment, the implantable pulse generator 10 is a pacemaker. Alternatively, the implantable pulse generator 10 is an implantable cardioverter/defibrillator. In one embodiment, the transvenous catheter 14 includes a transmission element 16, which is adapted to transmit mechanical signals. In one embodiment, the mechanical signals include signals in the ultrasonic frequency range. The system further includes an implantable pacing electrode 18. The implantable pacing electrode 18 receives the mechanical signals transmitted by the transmission element 16. In response to receiving the mechanical signals, the implantable pacing electrode 18 generates and/or produces electrical energy which this to be delivered between an anode and a cathode surface on the implantable pacing electrode 18. In one embodiment, mechanical signals from the transmission element 16 are transmitted to two or more implantable pacing electrodes 18.

In one embodiment, the implantable pulse generator 10 of the present subject matter is an implantable pacemaker.

Alternatively, the implantable pulse generator 10 of the present subject matter is an implantable cardiac defibrillator. In addition, the transvenous catheter 14 further includes one or more pacing electrodes and/or one or more defibrillation electrodes. One example is shown in FIG. 1 in which the transvenous catheter 14 is shown with a distal tip pacing electrode 24. Additional pacing/sensing electrodes can also be positioned along the body of the transvenous catheter 14 and coupled to the implantable pulse generator 10 to allow for additional pacing and sensing activity.

In one embodiment, the implantable pulse generator 10 includes input circuitry to receive cardiac signals sensed by pacing electrodes, such as pacing electrode 24. The input circuitry is coupled to morphology analyzing circuitry which analyzes cardiac signals received through the input circuitry. In one embodiment, one or more electrochemical batteries are housed within the implantable pulse generator 10 and supply electrical energy to output circuitry for delivering pacing level energy pulses to the pacing electrodes coupled to the transvenous catheter 14 under the control of the morphology analyzing circuitry. The implantable pulse generator 10 further includes transmission circuitry coupled to the output circuitry for supplying energy to the transmission element 16.

Upon receiving the energy from the transmission circuitry, the transmission element 16 produces one or more mechanical signals which are transmitted from the transmission element 16. In one embodiment, the transmission element 16 is a piezoelectric element which is adapted to cause mechanical energy to be delivered to the implantable pacing electrode 18 so as to allow the implantable pacing electrode 18 to generate and deliver one or more electrical pulses.

FIG. 1 shows one embodiment where the transmission element 16 is located along the body of the transvenous catheter 14. The transmission element 16 is positioned along the transvenous catheter 14 to allow for the transmission element 16 to be positioned in any number of locations within a heart which is accessible to a transvenous catheter 14. For example, the transmission element 16 is positioned along the catheter 14 to allow for the element 16 to be positioned within a right atrial chamber of the heart. In an alternative embodiment, the transmission elements 16 can be positioned along the transvenous catheter 14 to position the transmission element in any number of locations accessible to a transvenous catheter. For example, transmission element 16 can be located along the transvenous catheter 14 to position the transmission element in a supraventricular location of a heart. In an additional embodiment, the transmission element 16 may be located along the transvenous catheter 14 at or adjacent a distal end 32 of the transvenous catheter 14. Transvenous catheter 14 could then be inserted through the coronary sinus vein to locate the transmission element 16 adjacent to either the left atrial chamber of the left ventricular chamber of the heart.

The implantable pacing electrode 18 is adapted to receive mechanical energy transmitted from a transmission source which is external of the implantable pacing electrode 18. In one embodiment, the transmission source is the transmission element 16 located along the transvenous catheter 14. In an alternative embodiment, the transmission source is located within or on the housing 34 of the implantable pulse generator 10. In an alternative embodiment, the transmission source is located at a remote site which is neither on the transvenous catheter 14 or associated with the housing 34. Upon receiving the mechanical energy, the implantable pacing electrode 18 converts the mechanical energy into electrical energy. The electrical energy generated within the implantable pacing electrode 18 is then used to cause a pacing level electrical energy pulse to be delivered across an anode and a cathode position on the implantable pacing electrode 18.

In one embodiment, the mechanical signal is an ultrasonic signal transmitted from the transmission element 16. In one embodiment, the transmission element 16 is a piezoelectric element, where the piezoelectric element is coupled to the transmission circuitry located within the implantable pulse generator 10. The transmission circuitry is adapted to drive the transmission element 16 to produce an ultrasonic signal from the piezoelectric element. In one embodiment, the ultrasonic signal produced by the transmission element 16 is transmitted omnidirectionally. The directionality of ultrasonic transmission from a piezoelectric element depends on its physical dimensions (size and aspect ratio), its transmission mode (full wave, ¼ wave, etc.), and its coupling with the conduction medium. In one embodiment, the transmission element is constructed to transmit directionally and the ultrasonic signal produced by the transmission element 16 is directed in the direction of the implanted pacing electrode 18. In an alternative embodiment, the element is constructed to have less directional transmissions so that one or more pacing elements might be affected. In one embodiment, the transmission element delivers energy in a low frequency range, where a low frequency range is approximately one to five (1 to 5) megahertz, where one (1) megahertz is an acceptable value.

Besides being located on the catheter or within the housing of the implantable pulse generator 10, the transmission element 16 can be mounted within the header 36 of the implantable pulse generator 10. In a further embodiment, the transmission element 16 is coupled to the implantable pulse generator 10 through the use of an electrical lead, when the transmission element 16 is positioned subcutaneously in a position adjacent the heart of the patient.

In one embodiment, the implantable pacing electrodes 18 includes a piezoelectric element that is tuned to resonate in a specific frequency range. A transmission element 16 is provided that transmits ultrasonic frequencies in the resonance frequency range of the implantable pacing electrode 18. Upon receiving the ultrasonic signal, the piezoelectric element of the implantable pacing electrode 18 generates electrical energy which is used to cause a pacing level energy pulse to be delivered between an anode and a cathode on the implantable pacing electrode.

In an additional embodiment, more than one transmission element (e.g., more than one piezoelectric element) can be utilized in developing the ultrasonic signal to activate the implantable pacing electrode 18. For example, a first transmission element is positioned on the implantable pulse generator 10, and a second transmission element is positioned on the transvenous catheter 14. Alternatively, a first transmission element is located on or within the implantable pulse generator 10 and a second transmission element is coupled through a lead to the implantable pulse generator 10 and implanted subcutaneously adjacent to the heart. Other combinations of two or more transmission elements are also possible and considered within the scope of the present subject matter. Furthermore, each of the transmission elements can be adapted to transmit a signal at an individualized frequency range. For example, a first transmission element is adapted to transmit a first signal in a first frequency range and a second transmission element is adapted to transmit a second signal in a second frequency range. Each of the one or more elements 18 is then adapted to respond to the first and second frequency ranges as will be more fully described below.

Figure 2:
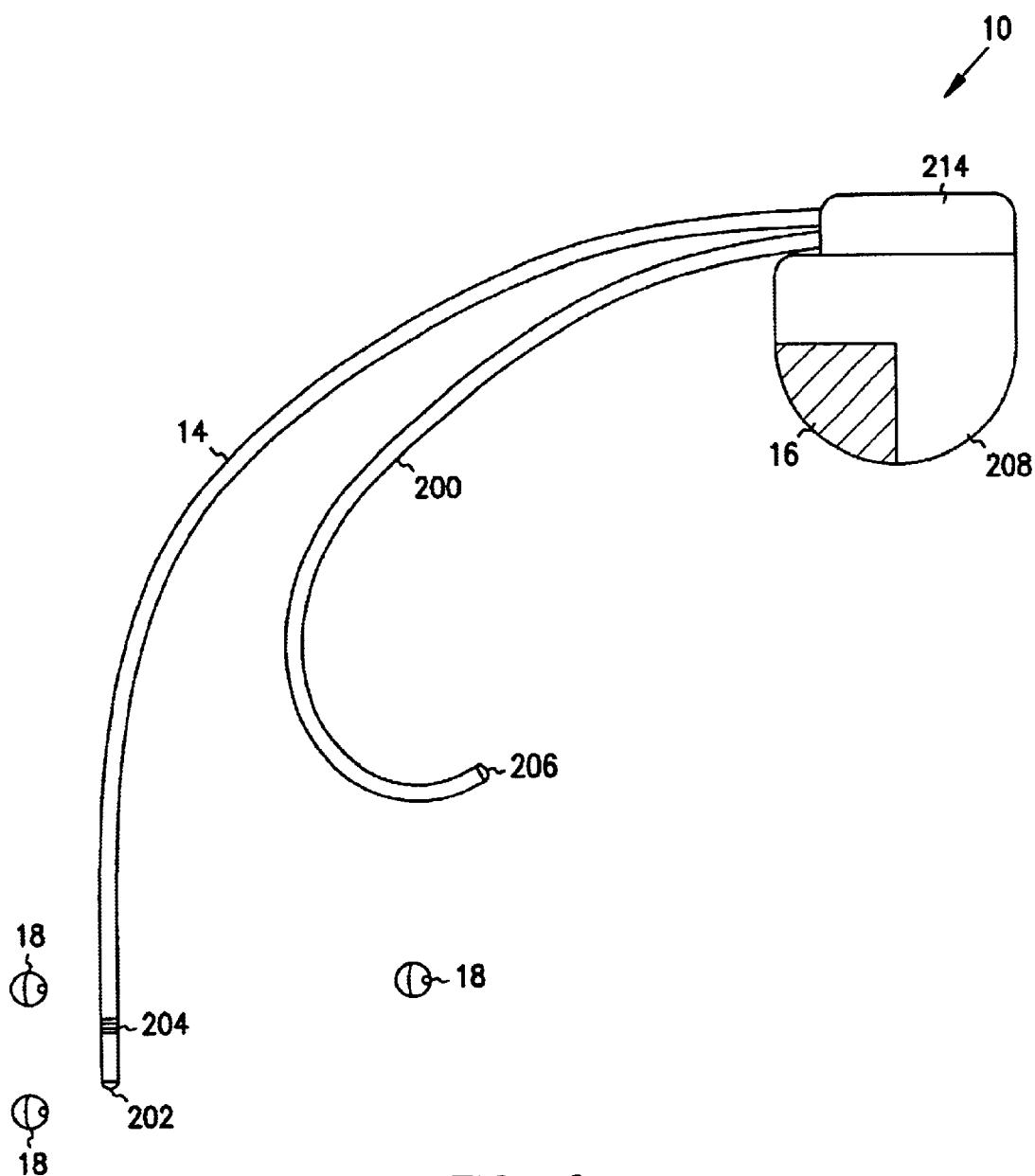
FIG. 2 shows one embodiment of a system according to the present subject matter.

Referring now to FIG. 2 there is shown an additional embodiment of the present subject matter. FIG. 2 shows the implantable pulse generator 10 coupled to the transvenous catheter 14 and to a second transvenous catheter 200. The second transvenous catheter 200 includes at least one pacing electrode physically and electrically coupled to the implantable pulse generator 10. In the embodiment, the second transvenous catheter 200 is implanted in the supraventricular region of the heart to allow for cardiac signals to be sensed from and pacing pulses to be delivered to the supraventricular region of the heart. In an alternative embodiment, the second transvenous catheter 200 is adapted to be implanted through the coronary sinus vein to position the pacing electrodes adjacent to the left atrium or to the left ventricular region of the heart. In an additional embodiment, the second catheter 200 can include two or more pacing electrodes, where such catheter structures are known and are considered to be within the scope of the present subject matter.

In one embodiment, the transvenous catheter 14 and the second transvenous catheter 200 are implanted into the heart and then coupled to the implantable pulse generator 10. The implantable pulse generator 10 is then implanted subcutaneously in the body. In one embodiment, the transvenous catheter 14 includes a distal tip pacing electrode 202 and a second pacing electrode 204. In one embodiment, the second pacing electrode 204 is an annular or semi-annular ring electrode which is positioned proximal to the distal tip of pacing electrode 202 to allow for bipolar pacing and sensing from the transvenous catheter 14. The second transvenous catheter 200 also includes a distal tip electrode 206. The distal tip electrode 206 can be used for unipolar sensing and pacing between the distal tip electrode 206 and the housing 208 of the implantable pulse generator 10.

In the embodiment of FIG. 2, the implantable pulse generator 10 is shown having the transmission element 16 associated with the housing 208 of the implantable pulse generator 10. In one embodiment, the transmission element 16 is positioned within the housing 208 of the implantable pulse generator 10. Additionally, the transmission element 16 can also be positioned on or within a connector block 214 of the implantable pulse generator 10. In addition to associating the transmission element 16 with the housing 208, matching layers of material are used in association with the transmission element 16 to improve the acoustic coupling between the piezo-electric crystal (one possible material for the transmission element 16) and the conducting medium (i.e., the body). Additionally, matching layers can be added to additional portions of the implantable pulse generator 10 which are in contact with tissue. Regardless of the position of the transmission element 16, the output of the transmission element 16 is directed towards the implantable pacing electrodes 18.

In the embodiment shown in FIG. 2, two or more implantable pacing electrodes 18 positioned within a transmission range of the transmission element 16. In one embodiment, the two or more implantable pacing electrodes 18 are implanted within a heart. When two or more implantable pacing electrodes 18 are used, each implantable pacing electrode 18 includes a piezoelectric element that is tuned to resonate at a different frequency. In one embodiment, this allows implantable pacing electrodes 18 to be selectively paced by transmitting mechanical signals of the implantable pacing electrode 18 specific resonate frequency from the transmission element 16. In one embodiment, a transmission element 16 can deliver a series of signals having different frequencies where each frequency triggers or causes separate implantable pacing electrode 18 elements to deliver pacing pulses to the heart 28. This type of configuration allows two or more implantable pacing electrodes 18 to deliver pacing pulses in an ordered or specific pattern. In one embodiment, selectively and sequentially activating two or more implantable pacing electrodes 18 allows the heart to contract in a more forceful and efficient matter.

In an additional embodiment, two or more implantable pacing electrodes 18 can be implanted in the supraventricular region and in the ventricular region of the heart. The implantable pacing electrodes 18 implanted in the supraventricular region can be tuned to resonate at a first frequency, and the implantable pacing electrodes 18 implanted in the ventricular region can be tuned to resonate at a second frequency. The transmission element 16 can then transmit a first signal to cause the implantable pacing electrodes 18 implanted in the atria to deliver a first pacing pulse. The transmission element 16 can subsequently deliver a second signal to cause the implantable pacing electrodes 18 implanted in the ventricular region to deliver a second pacing pulse. In addition to including multiple implantable pacing electrodes 18, two or more transmission elements 16 can be included with two or more implantable pacing electrodes 18. In one embodiment, each of the two or more transmission elements 16 can be tuned to deliver signals in frequency ranges that correspond to the different frequency ranges, or resonate frequencies of the implantable pacing electrodes 18. In this manner, each of the transmission elements 16 can be designated for one or more of the implantable pacing electrodes 18 implanted in the heart 28.

Figure 3:
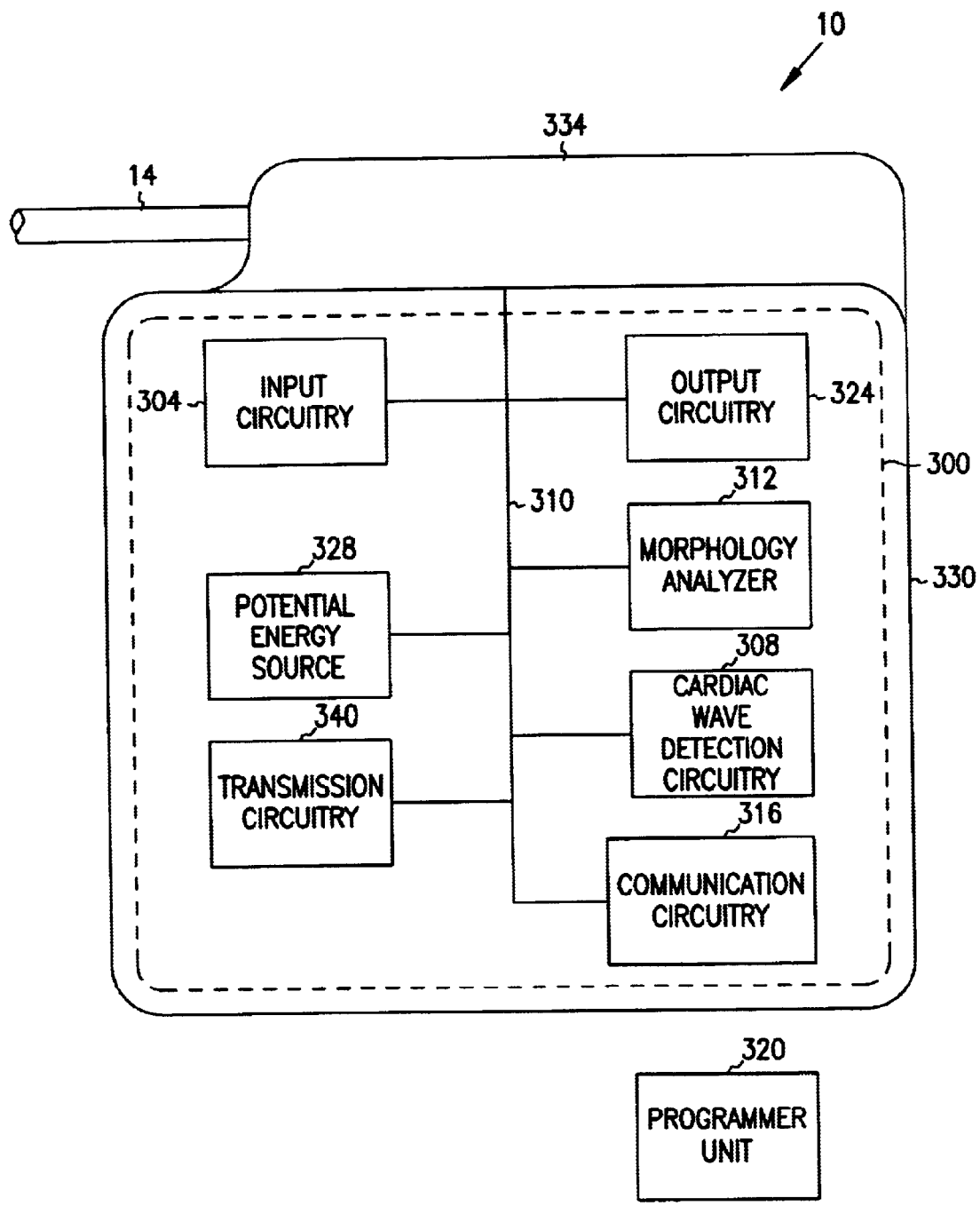
FIG. 3 shows one embodiment of a system according to the present subject matter.

Referring now to FIG. 3 there is shown an embodiment of a block diagram of an implantable pulse generator 10. The implantable pulse generator 10 includes electronic control circuitry 300 for receiving cardiac signals from the heart and delivering electrical energy to the heart. In one embodiment, pacing electrodes located on the transvenous catheter are electrically connected to input circuitry 304 by the lead conductors housed within the transvenous catheter 14. In one embodiment, the input circuitry 304 includes electrical surge protection circuitry and one or more amplifiers as are known. In one embodiment, the one or more amplifiers are electrically connected to cardiac wave detection circuitry 308 by bus 310. In one embodiment, the cardiac wave detection circuitry 308 includes an R-wave detector when a transvenous catheter is implanted in the right ventricle chamber of the heart. The cardiac wave detection circuitry 308 can also include a P-wave detector when a second transvenous catheter is implanted in the supraventricular region of the heart and then coupled to the implantable pulse generator 10. These components serve to sense and amplify the R-waves and P-waves of the heart and apply signals indicative thereof to morphology analyzing circuitry 312.

In one embodiment, the morphology analyzing circuitry 312 is a programmable microprocessor-based system, which contains memory circuitry having parameters for various pacing and sensing modes. The morphology analyzing circuits 312 also store data indicative of the cardiac signals received by the input circuitry 304. Communications circuitry 316 is additionally coupled to the morphology analyzing circuitry 312 by bus 310. Communications circuitry 316 allows the implantable pulse generator 10 to communicate with a programmer unit 320. In one embodiment, communications circuit 316 and the programmer unit 320 use a wire loop antenna and a radio frequency telemetry link, as is known in the art, to receive and transmit command signals and data to and from the programmer unit 320 and the electronic control circuitry 300. In this manner, programming commands or instructions are transferred to the electronic control circuitry 300 of the implantable pulse generator 10.

The morphology analyzing circuitry 312 responds to sense cardiac signals by providing signals to output control circuitry 324. In one embodiment, the output circuitry 324 provides pacing level electrical energy to the heart. Power to the implantable pulse generator 10 is supplied by a potential energy source 328 which is housed within the implantable pulse generator 10. In one embodiment, the potential energy source 328 is a electrochemical battery as is known in the art. The electronic control circuitry 300 further includes transmission circuitry 340. In one embodiment, transmission circuitry 340 controls the mechanical signals delivered by one or more of the transmission elements. In one embodiment, the transmission circuitry 340 controls which transmission element is activated, how long the transmission element is activated, and at what level of intensity the transmission element is activated. The transmission circuitry 340 is coupled to the electronic control circuitry 300 and receives command and control signals from the morphology analyzer 312 by bus 310. The morphology analyzing circuitry 312 responds to cardiac signals sensed within the heart by providing signals to either the output circuitry 324 or to the transmission circuitry 340 to cause pacing level energy pulses to be delivered to the heart through either the pacing electrodes attached to one or more transvenous catheters and/or the implantable pacing electrodes 18.

In one embodiment, the electronic control circuitry 300 of the implantable pulse generator 10 is encased and hermetically sealed in a housing 330 suitable for implanting in a human body. A connector block 334 is additionally attached to the housing of the implantable pulse generator 10 to allow for physical and electrical attachment of one or more transvenous catheters and the electrodes to the implantable generator 10 and the encased electronic control circuitry 300.

In one embodiment, the transvenous catheter 14 includes a distal tip pacing electrode. This allows the transvenous catheter to sense rate signals, or near field signals, from the ventricle region of the heart. In an alternative embodiment, two or more pacing electrodes can be included on the transvenous catheter 14 to allow for bipolar sensing and pacing. In an additional embodiment, pacing electrodes can be located on both a first transvenous catheter and a second transvenous catheter when two catheters are implanted into the heart. This allows for near field signals to be sensed both from the ventricle and the supraventricular region of the patient's heart. Other intracardiac catheter arrangements and configurations known in the art are also possible and considered to be within the scope of the present system.

Figure 4:
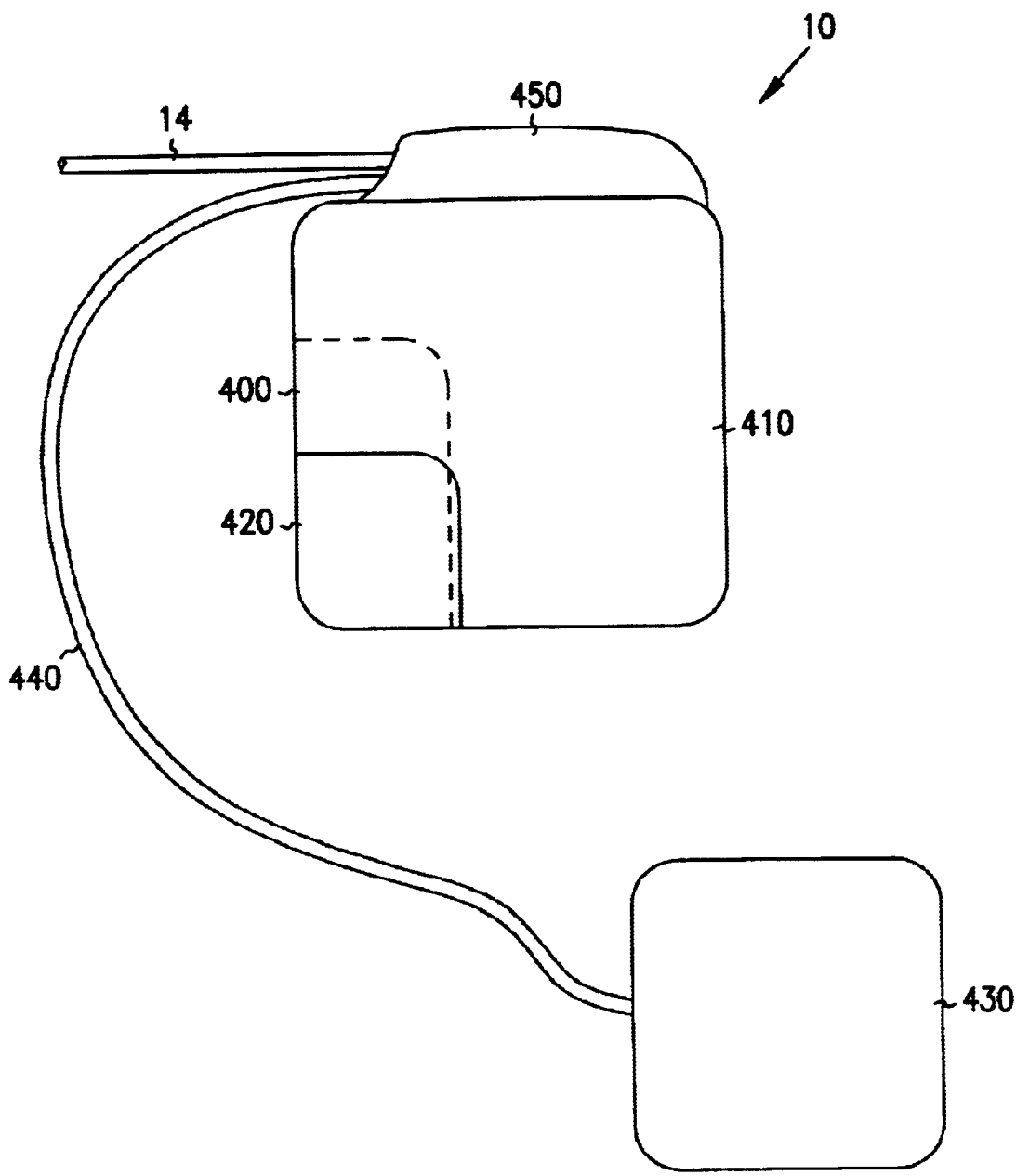
FIG. 4 shows one embodiment of a system according to the present subject matter.

Referring now to FIG. 4, there is shown several embodiments of a transmission element in association with an implantable pulse generator 10. In one embodiment, the transmission circuitry 340 is coupled to a transmission element 400 which is positioned within the housing 410 of the implantable pulse generator 10. The transmission element could also be positioned on an exterior portion of the housing 410 of the implantable pulse generator 10. A transmission element 430 is shown coupled to the transmission circuitry 340 through the use of a transmission lead 440. The transmission lead 440 physically and electrically couples the transmission element 430 to the transmission circuits 340 through the use of the connector block 450. The transmission element 430 can be implanted subcutaneously at a position adjacent the heart. Alternatively, the transmission element 430 can be positioned subcutaneously in any position that allows for the mechanical signal to best reach the implanted pacing electrodes of interest. As previously mentioned, one or more transmission elements can also be positioned within or on the connector block 450. Also, matching layers can be used in conjunction with the transmission element 430, as previously described.

Figure 5:
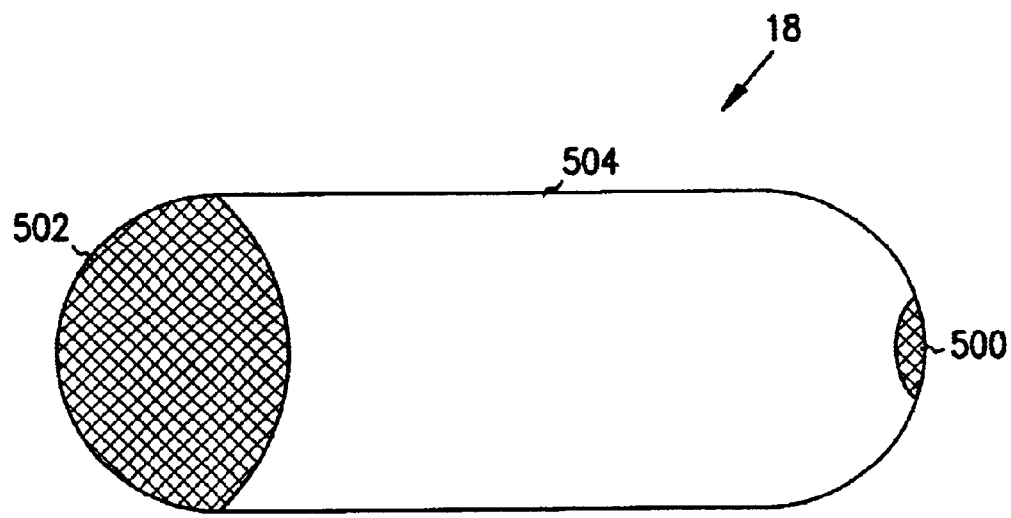
FIG. 5 shows one embodiment of an electrode according to the present subject matter.

Referring now to FIG. 5, there is shown an embodiment of the implantable pacing electrode 18. The implantable pacing electrode 18 includes a cathode 500 and an anode 502. The implantable pacing electrode 18 includes a housing 504. In one embodiment, the housing 504 is the piezoelectric element of the implantable pacing electrode 18. Alternatively, the piezoelectric element is contained within the housing 504. The piezoelectric element is adapted to receive mechanical energy and convert the mechanical energy into electrical energy where the mechanical energy originates from a source external to the implantable pacing electrode 18. In one embodiment, the external source is the transmission element 16 previously described. In an alternative embodiment, the external source is a source located outside of the patient's body. The electrical energy generated by the piezoelectric element then causes a pacing level energy pulse to be delivered between the cathode 500 and the anode 502.

The housing 504 is constructed of a material suitable for implanting into the human body. In one embodiment, the housing 504 is a cylinder, or elongate segment, of piezoelectric element, where circuitry for controlling the implantable pacing electrode 18 is contained within the cylinder. The piezoelectric element can also have matching layers to improve the acoustic coupling between the element of the electrode 18 and the tissue in which it is embedded. In an alternative embodiment, the piezoelectric and control circuitry are embedded in housing 504 which is constructed of an acoustically conductive material, such as an epoxy resin.

In an additional embodiment, implantable pacing electrode 18 includes an active fixation element. In one embodiment, the active fixation includes tines positioned on the peripheral surface of the electrode 18. Alteratively, a hook can be used, where the hook can have, or be, either the anode or cathode of the electrode 18. Additionally, the hook can include one or more barbs. In one embodiment, the electrode 18 is approximately five (5) to fifteen (15) millimeters in length (along longitudinal axis) and approximately one (1) to four (4) millimeters in diameter. In one embodiment, the electrode is six (6) millimeters in length and has a diameter of three (3) millimeters. Additionally, the electrode 18 can have any number of shapes including, but not limited to, spherical, tubular, cylindrical, and elliptical. In an alternative embodiment, the implantable pacing electrode 18 can have any shape that is suitable for housing the pacing control circuitry and the piezoelectric element, and which has a peripheral surface that is suitable to accept an anode and a cathode of sufficient size and shape to deliver pacing energy pulses.

In one embodiment, the piezoelectric element of the electrode 18 is tuned, or selected, to resonate in a low frequency range, where the low frequency range is approximately in the range of between 1–5 megahertz, where one megahertz is an acceptable value. Alternatively, the frequency range is approximately 250 kilohertz to 20 megahertz, where 750 kilohertz to 7.5 megahertz is a range to be used. Additionally, the pacing pulses generated by the implantable pacing electrode 18 are controlled by delivering short duration pulses of ultrasonic energy, where each pulse of ultrasonic energy is used to create a pacing level pulse by the implantable pacing electrode 18. For example, it is known that cardiac tissue may be stimulated with a small pacing pulse of 2 milliseconds that delivers 5 to 10 microjoules. If the receiver only received energy during the 2 millisecond pacing pulse duration, then it would need to receive 2.5 to 5 microjoules per millisecond which is a reception power of 2.5 to 5 milliwatts. Assuming no losses, if the receiver had a 30 square millimeter cross-sectional area (e.g., 5 millimeter wide by 6 millimeter long) and was 5 centimeter from an omni-directional transmitter, then the transmission power would need to be about 2.5 to 5 Watts. In one embodiment, the short duration pulses are programmable values in the range of 0.5 to 10 millisecond, where 2 milliseconds is an acceptable value.

In an alternative embodiment, instead of delivering the pacing pulses only while the ultrasonic transmission from the transmission unit is underway, the implanted pacing electrode 18 stores the received energy over time and then delivers that energy as a pacing pulse when the transmission is stopped (e.g., when the transmission has stopped for approximately 10 milliseconds, the stored energy is delivered as a pacing pulse). With a maximum pacing rate of approximately 180 beats/minute, the same no-losses calculations requires the transmission power to be about 30 milliwatts or less. In one embodiment, circuitry in the implanted pacing electrode that is powered by the stored energy, detects the presence of a period without transmissions and then delivers the stored energy as a pacing pulse. In one embodiment, the charging duration and transmission power is timed to a cardiac cycle so as to ensure that the implantable pacing electrode 18 is prepared to deliver a pacing pulse when necessary.

Figure 6:
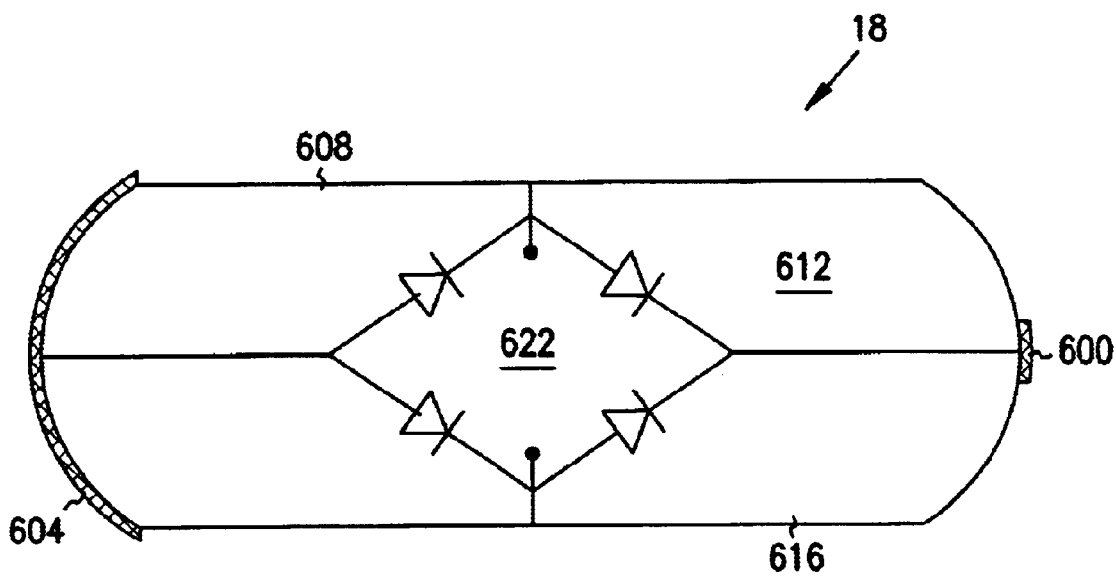
FIG. 6 shows one embodiment of an electrode according to the present subject matter.

Referring now to FIG. 6, there is shown one embodiment of the implantable pacing electrode 18 the present subject matter. In one embodiment, the implantable pacing electrode 18 includes a cathode 600 and an anode 604. The implantable pacing electrode 18 further includes a housing 608 that is suitable for implantation into the cardiac tissue of a human. As previously described, the housing 608 can be constructed of the piezoelectric element. The anode 604 and the cathode 600 are positioned on the peripheral surface of the housing 608. Mounted within the housing 608 is pacing control circuitry 612. The pacing control circuitry 612 is coupled to the anode 604 and the cathode 600 and the piezoelectric element, where in this embodiment the piezoelectric element is the housing 608. The piezoelectric element receives mechanical energy from a source external to the implantable pacing electrode 18 and generates electrical energy to cause a pacing level energy pulse to be delivered between the cathode 600 and the anode 604. In the present embodiment, a full wave bridge rectifier 622 is used with the piezoelectric element to generate the pacing level energy pulse.

Figure 7:
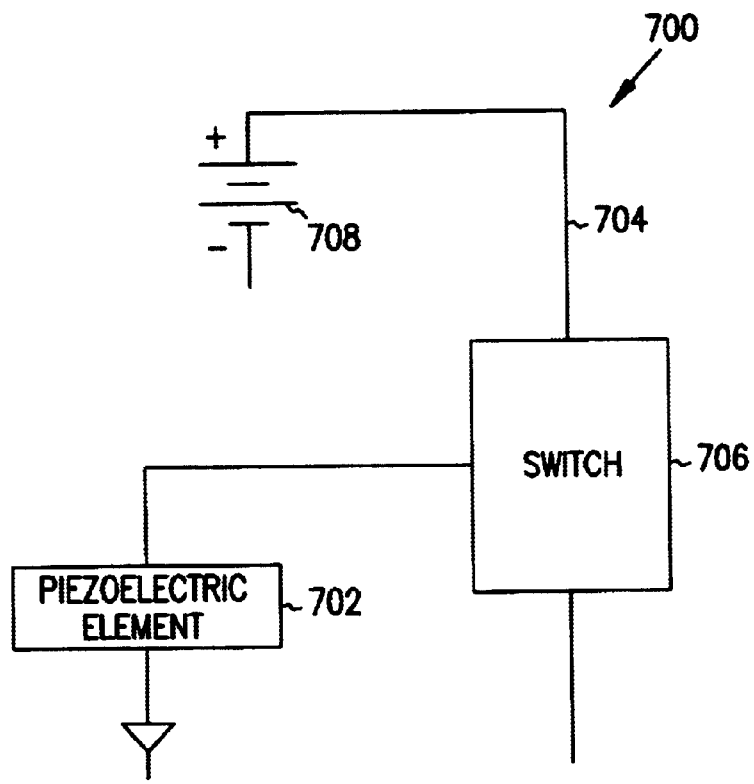
FIG. 7 shows a block diagram of one embodiment of the present subject matter.

Referring now to FIG. 7, there is shown an alternative embodiment of pacing control circuitry 700. In one embodiment, the pacing control circuitry 700 includes a piezoelectric element 702, where the piezoelectric element 702 is electrically coupled to the pacing control circuitry 700. The pacing control circuitry 700 further includes a switch 706 and a potential energy source 708. The piezoelectric element 702 and the potential energy source 708 are electrically coupled to the switch 706. In the present embodiment, the piezoelectric element 702 is used to generate a switching signal, where the switching signal is the electrical energy generated from the piezoelectric element 702. Upon receiving mechanical energy from a transmission element, the piezoelectric element 702 transmits the switching signal to the switch 706. After receiving the switching signal, the switch 706 is switched on, causing electrical energy to flow from the potential energy source 708 which causes a pacing level energy pulse to be delivered across the cathode and anode to the heart. In one embodiment, the switch 706 is a metal oxide semiconductor field effect transistor.

In one embodiment, the potential energy source 708 is an electrochemical battery. In an alternative embodiment, the potential energy source 708 is created by a half-cell potential difference between the metal of the anode and the metal of the cathode. In an alternative embodiment, the potential energy source 708 is a recharged on a beat-to-beat basis by the half-cell potential difference between the surrounding interstitial fluids and the metals of the anode and cathode. Metals useful for the present subject matter include, but are not limited to, platinum-iridium, titanium, gold, and/or stainless steel.

In a further embodiment, the pacing control circuitry includes a capacitor, where the electrical energy generated by the half cell potential is stored in the capacitor. The electrical energy stored in the capacitor is then delivered to the heart as a pacing pulse when the piezoelectric element delivers the switching signal to the switch 706. In an additional embodiment, the implantable electrode further includes a third electrode positioned on the peripheral surface of the implantable housing, where the third electrode is constructed of a metal that is different than the anode or the cathode metal. In one embodiment, the third electrode is composed of a metal that provides a larger half cell potential between the anode or the cathode than is possible between the cathode and anode.

In an additional embodiment, the implantable pacing electrode 18 includes two piezoelectric elements, where each piezoelectric element has a different resonance frequency. The two piezoelectric elements are coupled to the pacing control circuitry where the first piezoelectric element and the second piezoelectric element can receive mechanical signals from the transmission element, or elements, to charge the capacitor. In one embodiment, the transmission element, or elements, alternates transmitting ultrasonic energy that is suitable for resonating the first piezoelectric element and transmitting ultrasonic energy that is suitable for resonating the second piezoelectric element. In other words, the transmission element sends out ultrasonic frequencies that alternate between frequencies that resonate the first piezoelectric element and the second piezoelectric element. As each of the piezoelectric elements are excited they generate electrical energy to charge the capacitor which is coupled within the pacing control circuitry.

When a pacing pulse is to be delivered to the heart, the transmission element(s) delivers ultrasonic energy at a frequency that will resonate both the first piezoelectric element and the second piezoelectric element simultaneously. When both piezoelectric elements are excited simultaneously, the signals are then used to activate the switch 706 causing the energy stored in the capacitor to be delivered and pace the cardiac tissue of the patient. It is recognized that the two frequencies would need to be sufficiently different so that ultrasonic energy delivered at a first frequency to resonate a first piezoelectric element would not significantly effect a second piezoelectric element that is adapted to resonate at a second frequency. As such, the resonant frequency of the first and the second piezoelectric element must not be harmonics of each other. In addition, requiring both first and second piezoelectric elements to be stimulated simultaneously in order to deliver the pacing pulses, adds a safety feature to the implantable pacing electrode 18, as the chances of having an external source of mechanical energy capable of resonating both the first and the second piezoelectric elements simultaneously is significantly less than encountering a single external source that would resonate either the first or the second piezoelectric element.

In an alternative embodiment, the first frequency is used to cause the first piezoelectric element to charge the capacitor. The second frequency is then used to control a switch to cause the capacitor to supply a pacing level pulse to the anode and cathode of the implantable pacing electrode 18. One aspect to this use of a second frequency is that the risk of inappropriate release by external ultrasonic sources is reduced since the external source would now need to match two dissimilar frequencies instead of just one. For these concepts, the implanted device would be adapted to produce ultrasonic transmissions at both frequencies.

In a further embodiment, the implantable pacing electrode 18 has two or more piezoelectric elements, where each piezoelectric element has a different resonance frequency. The two piezoelectric elements are coupled to the pacing control circuitry where each of the two or more piezoelectric elements receive mechanical signals from the transmission element, or elements, to charge the capacitor. In one embodiment, the transmission element, or elements, continuously transmit ultrasonic energy that is suitable for resonating each of the piezoelectric elements. As each of the piezoelectric elements are excited they generate electrical energy to charge the capacitor which is coupled within the pacing control circuitry.

In one embodiment, when a pacing pulse is to be delivered to the heart one or more of the transmission elements stop transmitting for a predetermined time interval. In one embodiment, a switch coupled to the piezoelectric elements and the discharge capacitor monitors the continuous flow of energy from the piezoelectric elements. When the flow of one or more of the elements is interrupted for more than the predetermined time interval the switch triggers the capacitor to discharge a pacing level pulse of energy between the anode and cathode of the implantable pacing electrode 18.

Alternatively, the switch is adapted to monitor the ultrasonic transmission for breaks, or interruptions, in the ultrasound transmission. When the switch detects an interruption in the transmission greater than the predetermined time interval the switch controls the capacitor to discharge a pacing level pulse of energy between the anode and cathode of the implantable pacing electrode 18. In one embodiment, the predetermined time interval is a programmable value in the range of ten (10) to fifty (50) milliseconds, with 10 milliseconds being an acceptable value.

In an additional embodiment, the switch controls the capacitor to supply a pacing pulse once the switch detects a sudden increase of ultrasonic intensity in one or more of the multiple frequencies. Alternatively, the switch detects sudden increases in the energy output of one or more of the piezoelectric elements due to a sudden increase of ultrasonic intensity in one or more of the multiple frequencies. Once the switch detects one or more of these sudden increases, it controls the capacitor to supply pacing pulses. Alternatively, the switch could be adapted to detect a combination of breaks and increases at the different frequencies which would signal a pacing pulse is to be delivered. Finally, a transmission at an entirely different frequency which creates a signal from an additional piezoelectric element could be used to trigger the delivery of a pacing pulse.

Figure 8:
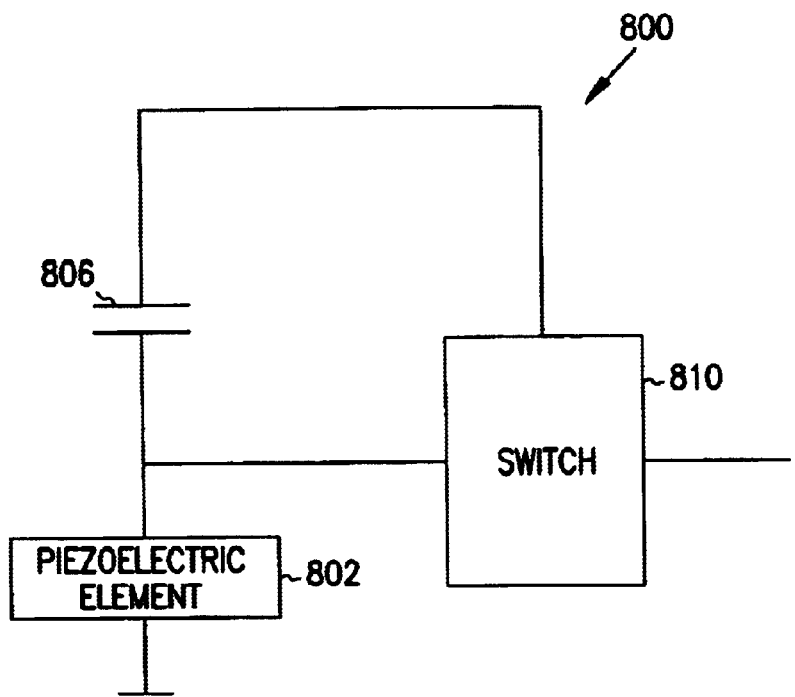
FIG. 8 shows a block diagram of one embodiment of the present subject matter.

Referring now to FIG. 8, there is shown an additional embodiment of the present subject matter. As previously discussed, the implantable pacing electrode 18 had been controlled by activating the ultrasound transmission for a short duration (about two milliseconds) to generate and deliver a pacing level pulse and then off for the remainder of the cardiac cycle. In the present embodiment, the ultrasound transmission is continuous so as to provide a continuous source of mechanical energy (or power) to the receiving element, or elements, within the implantable pacing electrode 18.

FIG. 8 shows one embodiment of pacing control circuitry 800, which includes at least one piezoelectric element 802. The pacing control circuitry 800 further includes a capacitor 806 and a switch 810. In one embodiment, the capacitor 806 is adapted to store the electrical energy generated as the piezoelectric element 802 receives the continuous ultrasound transmissions. The energy stored in the capacitor 806 is then used to provide pacing pulses across the anode and cathode of the implantable pacing electrode 18. In one embodiment, the energy from the capacitor 806 is used to deliver the pacing level pulses when the continuous ultrasound transmission to the piezoelectric element 802 is interrupted for a predetermined time interval. In one embodiment, the switch 810 monitors the continuous flow of energy from the piezoelectric element 802. When the flow is interrupted for more than the predetermined time interval the switch 810 triggers the capacitor 806 to discharge a pacing level pulse of energy between the anode and cathode of the implantable pacing electrode 18.

Alternatively, the switch 810 is adapted to monitor the ultrasonic transmission for breaks, or interruptions, in the ultrasound transmission. When the switch 810 detects an interruption in the transmission greater than the predetermined time interval the switch 810 controls the capacitor 806 to discharge a pacing level pulse of energy between the anode and cathode of the implantable pacing electrode 18. In one embodiment, the predetermined time interval is as previously described.

In an additional embodiment, it is possible to use two or more frequencies in a multiplexed fashion, where each of the frequencies resonates a separate piezoelectric element contained within two or more implantable pacing electrodes 18. The ultrasonic transmissions at the different frequencies are interleaved thus sharing the burden of charging the capacitor element in each implantable pacing electrode 18. The triggering of the pacing electrode 18 to deliver pacing pulses is then accomplished by simultaneously transmitting a combination of frequencies which is specific for signaling an individual implantable pacing electrode 18 to deliver a pacing pulse.

Figure 9:
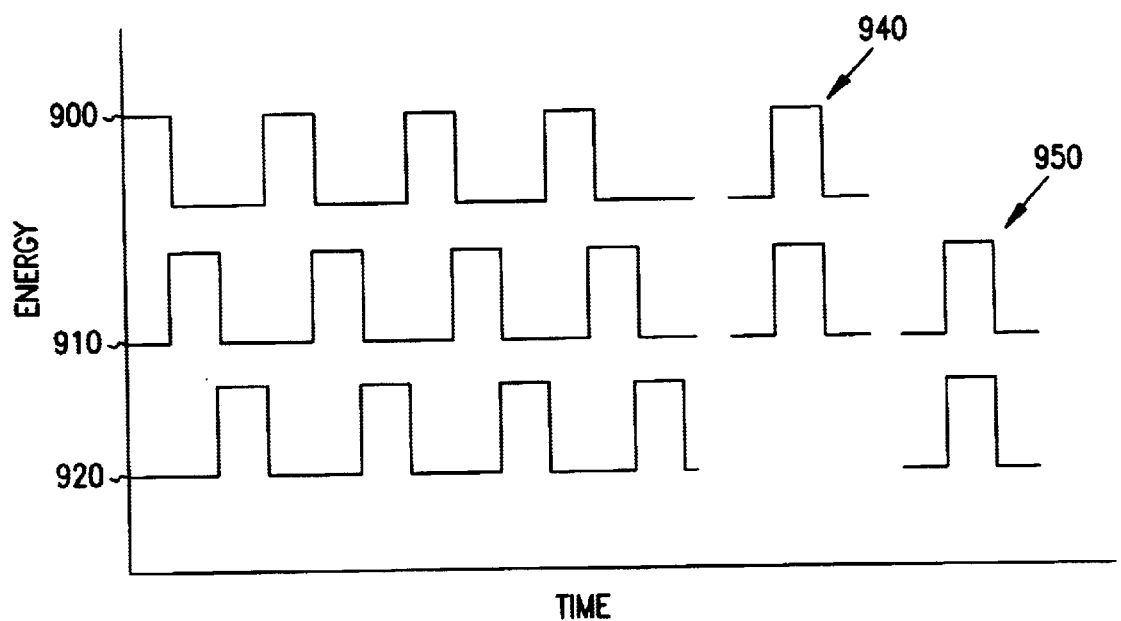
FIG. 9 shows embodiments of transmissions according to the present subject matter.

Referring now to FIG. 9, there is shown an embodiment of the present subject matter. FIG. 9 shows a representation of a first ultrasonic transmission 900, a second ultrasonic transmission 910, and a third ultrasonic transmission 920 being transmitted to a first, second and third implantable pacing elements. At 900, the first ultrasonic transmission is shown being pulsed at a first frequency, where the first frequency resonates the first implantable pacing element within each of the transmission elements causing it to generate electrical energy. At 910, the second ultrasonic transmission is shown being pulsed at a second frequency, where the second frequency resonates the second implantable pacing element within each of the transmission elements causing it to generate electrical energy. Finally, at 920 the third ultrasonic transmission is shown being pulsed at a third frequency, where the third frequency resonates the third implantable pacing element within each of the transmission elements causing it to generate electrical energy. In one embodiment, the first, second and third ultrasonic transmissions are staggered so that at any given time only one transmission is occurring, but the overall effect is to cause a continuous flow of electrical energy to be generated by the implantable pacing element.

Each of the transmissions serve to resonate one of the three piezoelectric elements in each of three implantable pacing elements. This results in the charging of the capacitor in each of the implantable pacing elements. When the implantable pacing elements are to be used to deliver pacing pulses different combinations of two of the frequencies are used to trigger the implantable pacing elements to deliver a pacing pulse. For example, the first implantable pacing element is triggered to deliver a pacing pulse when the first ultrasonic transmission 900 and the second ultrasonic transmission occur together 910, as shown at 940. In the same manner, the second implantable pacing element is triggered to deliver a pacing pulse when the second ultrasonic transmission 910 and the third ultrasonic transmission 920 occur together, as shown at 950. Finally, the implantable pacing element is triggered to deliver a pacing pulse when the first ultrasonic transmission 900 and the third ultrasonic transmission 920 occur together. This embodiment, therefore, allows for pacing to occur at two or more remote sites, where each of the remote pacing sites can be individually controlled by the combination of ultrasonic transmissions.

Alternatively, two or more implantable elements could be implanted in the same general location within the heart. By providing each of the two or more implantable elements with three or more piezoelectric elements that have individual resonance frequencies, ultrasonic transmissions can be delivered to continuously charge the capacitors. Additionally, each element can also be individually controlled to provide a pacing pulse. This allows for a first element to be discharged while the second element continues to charge. The first element then "skips" the next required pacing pulse as the second element is triggered to deliver the pulse. This allow for a longer time (e.g., a two cardiac cycle charging time) for each of the elements to prepare for delivering a pacing pulse. When three elements are used in a particular location, the present embodiment would allow for a three cardiac cycle charging time.

The energy that is accumulated and then triggered for release as a pacing stimulus does not necessarily need to come from the ultrasonic source in the implanted device. Rather it could be locally at the remote pacing element. For example, the mechanical action of the contracting heart could be utilized to produce electrical energy by compressing or deflecting a piezoelectric element that would serve to produce the charge for storage in a capacitor. It is also possible that high-frequency (10 to 50 kHz) low-voltage AC electrical signals could be passed over the heart by the implanted device. Because of the high-frequency, and low voltages, these signals would not excite the myocardial tissue. However, the remote pacing site could rectify the signals locally and use it as an energy source for charging a capacitor. In this arrangement, it makes sense for the two (or more) electrodes at the remote pacing site to be further apart so as to capture as much of the high-frequency AC field as possible. This could be accomplished by having the electrodes in the forms of short flexible wires.

What is claimed is:

1. A system comprising:
    a first piezoelectric element which converts mechanical energy into electrical energy, the mechanical energy which originates from a source external to an implantable electrode;
    a cathode and an anode, where electrical energy generated by the first piezoelectric element causes a pacing level energy pulse to be delivered between the anode and the cathode; and
    an implantable housing which includes a peripheral surface, where the first piezoelectric element is integrated with the housing, and the anode and the cathode are positioned at opposite sides on the peripheral surface of the housing.

2. The system of claim 1, further comprising pacing control circuitry coupled to the first piezoelectric element, the anode and the cathode such that the pacing control circuitry receives electrical energy generated by the first piezoelectric element and delivers pacing pulses between the anode and the cathode.

3. The system of claim 1, wherein the implantable housing includes an active fixation element.

4. A system comprising:
    a first piezoelectric element which converts mechanical energy into electrical energy, the mechanical energy which originates from a source external to an implantable electrode;
    a cathode and an anode, where electrical energy generated by the first piezoelectric element causes a pacing level energy pulse to be delivered between the anode and the cathode;
    pacing control circuitry coupled to the first piezoelectric element, the anode and the cathode, where the pacing control circuitry receives electrical energy generated by the first piezoelectric element and delivers the pacing level energy pulse between the anode and the cathode;
    where the pacing control circuitry includes:
        a switch, where the switch is operated by the electrical energy generated by the first piezoelectric element; and
        a potential energy source, where the potential energy source is coupled to the switch and supplies electrical energy to be delivered between the anode and the cathode once the first piezoelectric element provides electrical energy to activate the switch.

5. The system of claim 4, wherein the potential energy source is an electrochemical battery.

6. The system of claim 4, wherein the switch is a metal oxide field effect transistor.

7. A system comprising:
    a first piezoelectric element which converts mechanical energy into electrical energy, the mechanical energy which originates from a source external to an implantable electrode;
    a cathode and an anode, where electrical energy generated by the first piezoelectric element causes a pacing level energy pulse to be delivered between the anode and the cathode;
    pacing control circuitry coupled to the first piezoelectric element, the anode and the cathode, where the pacing control circuitry receives electrical energy generated by the first piezoelectric element and delivers the pacing level energy pulse between the anode and the cathode; and
    an implantable housing having a peripheral surface, where the pacing control circuitry is mounted within the housing, the first piezoelectric element is integrated with the housing, and the anode and the cathode are positioned at opposite sides on the peripheral surface of the housing.

8. The system of claim 7, wherein the implantable housing includes a second piezoelectric element which converts mechanical energy into electrical energy.

9. The system of claim 8, wherein the second piezoelectric element has a different resonance frequency than the first piezoelectric element.

10. A system comprising:
- a first piezoelectric element which converts mechanical energy into electrical energy, the mechanical energy which originates from a source external to an implantable electrode;
- a cathode and an anode, where electrical energy generated by the first piezoelectric element causes a pacing level energy pulse to be delivered between the anode and the cathode;
- a second piezoelectric element which converts mechanical energy into electrical energy, where the first piezoelectric element resonates at a first frequency range and the second piezoelectric element resonates at a second frequency range; and
- a switch and a capacitor, where the switch is coupled to the first piezoelectric element, the second piezoelectric element, the anode and the cathode, and the capacitor is coupled to the switch, where electrical energy is generated by the first piezoelectric element when a first transmission at the first frequency range resonates the first piezoelectric element and electrical energy is generated by the second piezoelectric element when a second transmission at the second frequency range resonates the second piezoelectric element, where the electrical energy is stored in the capacitor and the switch causes the pacing level energy pulse to be delivered between the anode and the cathode when a predetermined pulse signal is detected.

11. The system of claim 10, where the predetermined pulse signal is a predetermined frequency change in the first frequency range.

12. The system of claim 10, where the predetermined pulse signal is a predetermined frequency change in the first and second frequency ranges.

13. A system comprising:
- a first piezoelectric element which converts mechanical energy into electrical energy, the mechanical energy which originates from a source external to an implantable electrode;
- a cathode and an anode, where electrical energy generated by the first piezoelectric element causes a pacing level energy pulse to be delivered between the anode and the cathode; and
- where the source includes a catheter having a transmission element adapted to transmit the mechanical signals to the first piezoelectric element, and a pulse generator, where the pulse generator includes a transmission circuit and where the transmission element is coupled to the transmission circuit to generate and transmit the mechanical energy to the first piezoelectric element.

14. The system of claim 13, where the transmission element transmits energy in a low frequency range of approximately one to five megahertz.

15. A method, comprising:
- transmitting mechanical energy from a source external an implantable electrode;
- receiving the mechanical energy within the implantable electrode;
- generating electrical energy within the implantable electrode from the mechanical energy;
- delivering pacing level energy pulse across an anode and a cathode positioned on the implantable electrode when the electrical energy is generated; and
- where causing the pacing level energy pulse includes:
  - generating a switching signal from the electrical energy;
  - transmitting the switching signal to a switch coupled to a potential energy source; and
  - receiving the switching signal to activate the switch.

16. The method of claim 15, wherein delivering pacing level energy pulses across the anode and the cathode includes causing energy stored in a capacitor to be delivered to the anode and the cathode once the switch has been activated.

17. The method of claim 15, wherein delivering pacing level energy pulses across the anode and the cathode includes using energy created by the half-cell potential difference between metal of the anode and metal of the cathode.

* * * * *